US00PP28122P3

(12) United States Plant Patent
Randag

(10) Patent No.: US PP28,122 P3
(45) Date of Patent: Jun. 13, 2017

(54) CALLA LILY PLANT NAMED 'SNOW STORM'

(50) Latin Name: *Zantedeschia sprengeri*
Varietal Denomination: Snow Storm

(71) Applicant: Sande B.V., 't Zand (NL)

(72) Inventor: Cecilius Jan-Jochem Randag, 't Zand (NL)

(73) Assignee: Sande B.V., 't Zand (NL)

( * ) Notice: Subject to any disclaimer, the term of this patent is extended or adjusted under 35 U.S.C. 154(b) by 94 days.

(21) Appl. No.: 14/544,432

(22) Filed: Jan. 6, 2015

(65) Prior Publication Data

US 2016/0198618 P1 Jul. 7, 2016

(51) Int. Cl.
*A01H 5/02* (2006.01)

(52) U.S. Cl.
USPC ..... Plt./490

(58) Field of Classification Search
USPC ..... Plt./490
See application file for complete search history.

(56) References Cited

PUBLICATIONS

UPOV—International Union for the Protection of New Varieties of Plants: PLUTO Plant Variety Database; May 19, 2016; cultivar name—'Snow Storm' (1 pg).*

* cited by examiner

*Primary Examiner* — Susan McCormick Ewoldt
(74) *Attorney, Agent, or Firm* — The Webb Law Firm

(57) ABSTRACT

'Snow Storm' is a new variety of *calla* lily having inflorescences with a white-colored spathe that produces 5-20 inflorescences per tuber. The inflorescence stems are about 35 cm in height. The leaves are green with whitish spots and have a leathery texture.

2 Drawing Sheets

Botanical classification: *Zantedeschia sprengeri*.
Varietal denomination: 'SNOW STORM'.

BACKGROUND OF THE NEW PLANT

The present invention comprises a new and distinct cultivar of *calla* lily, botanically known as *Zantedeschia sprengeri* and hereinafter referred to by the cultivar name 'Snow Storm'.

'Snow Storm' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of a *Zantedeschia sprengeri* seedling referred to as Z041613-632 (female parent, unpatented) with a *Zantedeschia sprengeri* seedling referred to as Z051287 (male parent, unpatented). 'Snow Storm' was selected in 2009 by the inventor in 't Zand, The Netherlands as one flowering plant within the progeny of the stated cross.

The first act of asexual reproduction of 'Summer Snow' by tissue culture was performed by the inventor in September of 2009 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown in a 14 cm pot at 12-14 weeks after planting in 't Zand, The Netherlands under greenhouse conditions, which approximate those generally used in horticultural practice. Color references are made to The 2001

R.H.S. Colour Chart of The Royal Horticulture Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Snow Storm' which, in combination, distinguish this *calla* lily as a new and distinct cultivar:

1. White-colored spathe without a pink blush;
2. Green-colored leaves with numerous white linear markings; and
3. High inflorescence production.

Further, when compared to *calla* lily plant named 'Chrystal Blush' (unpatented), 'Chrystal Blush' has a white spathe color with a blush (R.H.S. values unknown), and such blush is absent with 'Snow Storm'. Additionally, when compared to *calla* lily plant named 'Captain Ventura' (U.S. Plant Pat. No. 21,245), the upper surface spathe color of 'Captain Ventura' varies between Yellow-Green Group RHS 150D and Green-White Group RHS 157C, whereas the upper surface spathe color of 'Snow Storm' varies between White Group RHS 155A and 155D.

Table 1 provides similarities and differences of 'Snow Storm' to its parents, *Zantedeschia sprengeri* seedlings Z041613-632 and Z051287.

TABLE 1

| 'Snow Storm' | Similarities | Differences |
|---|---|---|
| Z041613-632 | Spathe shape | Spathe color (Between Yellow-White Group RHS 158D and 159D)<br>Spathe without pink blush<br>Plant height (10-50 cm) |
| Z051287 | Number of inflorescences | Spathe shape (Funnel)<br>Spathe color (Between Green-White Group RES 157D and White Group RHS N155A) |

BRIEF DESCRIPTION OF THE DRAWINGS

The accompanying photographic drawings illustrate the new variety at 12-14 weeks after planting, with the colors being as nearly true as is possible with color illustrations of this type.

DESCRIPTION OF THE PLANT

The Plant

Figure 1:
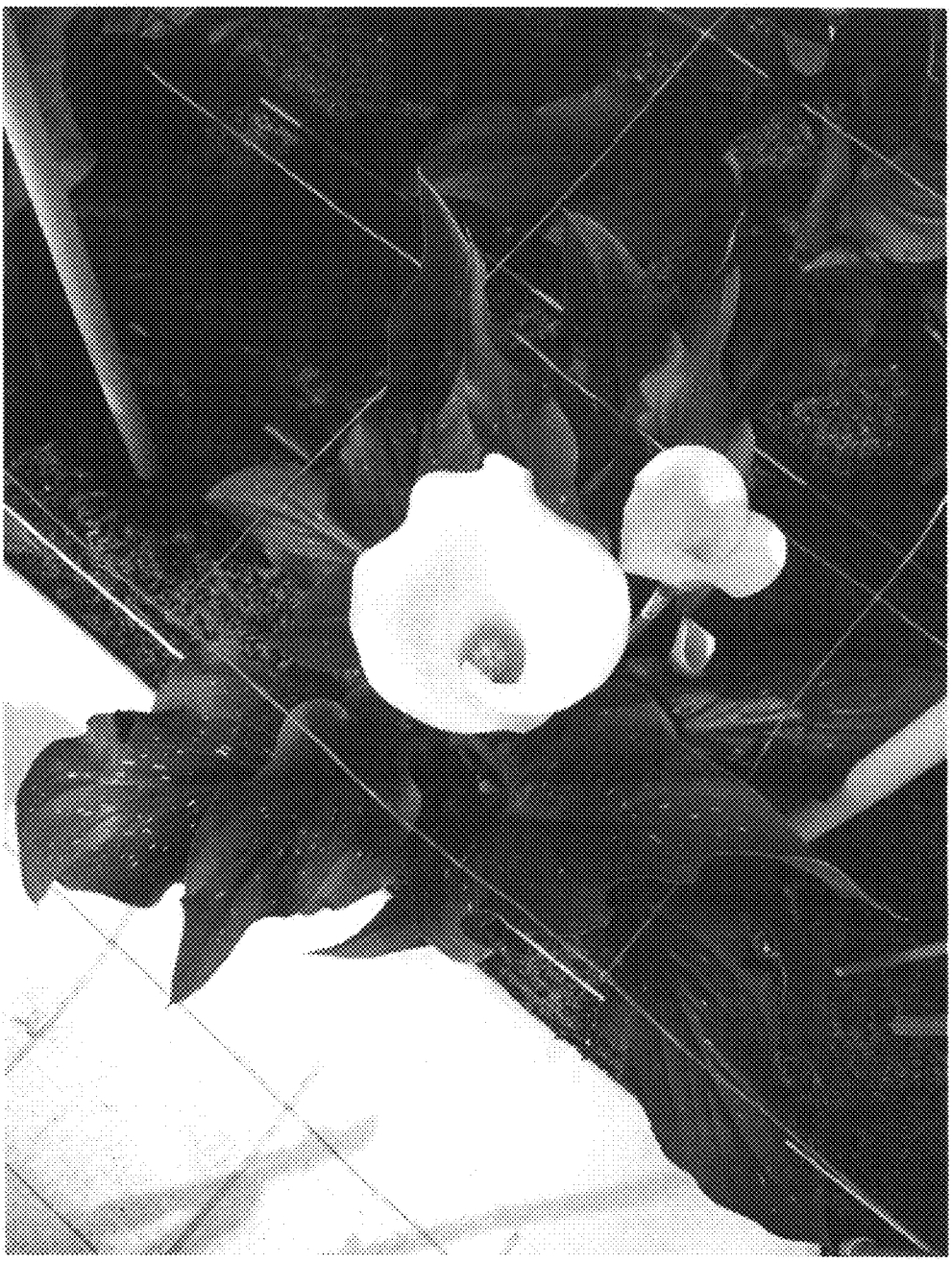
FIG. 1 is a photograph of an overhead view of a plant of the new variety.
Figure 2:
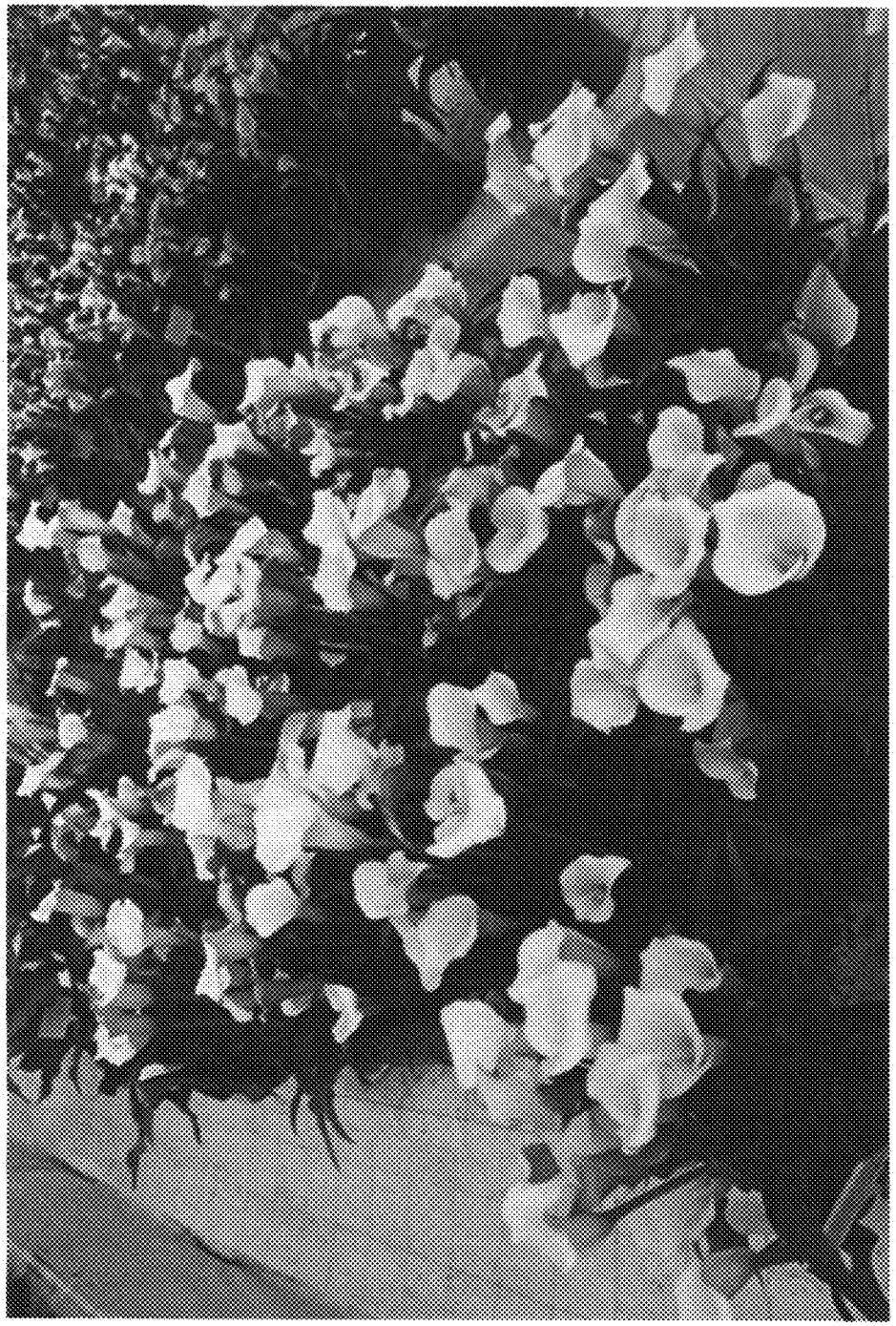
FIG. 2 is a photograph of a group of multiple plants of the new variety.

Size:

*Height of the leaf canopy above the soil.*—3-40 cm.

*Height of top of inflorescence above the soil.*—15-40 cm.

*Diameter.*—15-45 cm.

Form: Erect.

Number of inflorescences per tuber:

*Size* 14-16 *cm in diameter.*—5-8 inflorescences.

*Size* 16-18 *cm in diameter.*—6-15 inflorescences.

*Size* 18-20 *cm in diameter.*—7-20 inflorescences.

Branches:

*Character.*—Many (from 3-8); like the variety 'Odessa' (U.S. Plant Pat. No. 18,833). Color: Between Green Group RHS 143A and 143B.

Leaves:

*Size.*—Width: 2-10 cm. Length: 8-25 cm.

*Number per plant.*—15-30.

*Shape.*—Lanceolate.

*Color.*—Upper surface: Green Group RHS 137A to 137B, with transparent White Group RHS 155A and N155A spots. Lower surface: Green Group RHS 137A to 137B, with transparent White Group RHS 155A and N155A spots.

*Apex.*—Acuminate.

*Base.*—Attenuate.

*Margin.*—Undulate; having a color of Green Group RHS 137A to 137B.

*Veins.*—Configuration: Pinnate. Color: Green Group RHS 143A to 143B.

*Surface quality.*—Leathery.

*Petiole.*—Length: 3-20 cm. Diameter: 10 mm. Color: The base is White Group RHS 155A, and the upper part is Green Group RHS 143A and 143B.

Roots:

*Color.*—White.

*Branching.*—Similar to other *Zantedeschia* varieties.

The Inflorescence and Seeds

Spathe:

*Size.*—Length (measured from base opening to tip): 5-10 cm. Width: 3.5-7 cm. Height: 4-8 cm.

*Color.*—Upper surface: Varies between White Group RHS 155A and 155D. Lower surface: Varies between Green Group RHS 143B and 143C.

*Vein color.*—Between White Group RHS 155A and 155D.

*Shape.*—Cupped.

*Apex.*—Acute.

*Base.*—Rounded.

*Texture.*—Smooth (Upper and lower surfaces).

Spadix:

*Size.*—Length: 25-50 mm. Diameter: 3-12 mm.

*Color.*—Between Yellow Group RHS 8A and 8C.

*Position relative to spathe.*—Upright.

Peduncle:

*Size.*—Length: 15-35 cm. Diameter: 4-12 mm.

*Color.*—The upper part is between Yellow-Green Group RHS 144A and 144B, and the lower part is Green-White Group RHS 157C.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: More than 20. Pollen amount: Abundant and similar to 'Picasso' (U.S. Plant Pat. No 15,282), but not quantifiable due to minute pollen size. Color: Between White Group RHS 155A and 155B.

*Anther.*—Shape: Round. Length: Less than 1 mm. Color: Between Yellow Group RHS 8A and 8C.

*Filament.*—Length: Less than 1 mm. Color: Between White Group RHS 155A and 155B.

*Pistil.*—Number: 15 to 30. Length beyond perianth: About 1 mm.

*Stigma.*—Shape: Round. Size: Less than 1 mm.

*Style.*—Length: Less than 1 mm. Color: Between Yellow Group RHS 8C and 8D.

*Ovaries.*—Texture: Smooth. Length: Between 1 to 10 mm. Width: Between 1 to 10 mm. Color: Top color is between Yellow-Green Group RHS 145B and 145D, bottom color is from White Group RHS 155B to Green-White Group RHS 157C.

Seeds:

*Length.*—4-7 mm.

*Width.*—3-6 mm.

*Color.*—Between Yellow-Green Group RHS 150A and 151 A.

*Amount.*—Between 1-60.

Fruit:

*Amount.*—Multiple berries produced.

*Shape.*—Irregular.

*Color*.—Varies between Green Group RHS N143A to Yellow-Green Group RHS 145C.

General

Disease resistance: No unusual susceptibility to diseases noticed to date.
Pest resistance: No unusual susceptibility to pests noticed to date.
Heat tolerance: No heat tolerance.
Hardiness: Not hardy.
Flowering: Tubers planted in a greenhouse in The Netherlands in February produce inflorescences in April. Tubers planted outdoors in The Netherlands in May produce inflorescences in July. In general, the time from planting to first flowering takes eight weeks. However, tubers stored for a longer period before planting may flower earlier—up to five weeks after planting.
Lastingness: About two weeks on the plant.
Fragrance: None.

I claim:

1. A new and distinct variety of *calla* lily named 'Snow Storm' plant as herein described and illustrated.

* * * * *